(12) United States Patent
Young et al.

(10) Patent No.: US 7,740,648 B2
(45) Date of Patent: Jun. 22, 2010

(54) LOCKING BONE PLATE

(75) Inventors: Robert Allan Young, Downingtown, PA (US); Patrick Michel White, West Chester, PA (US); Michael Khowaylo, Mahwah, NJ (US)

(73) Assignees: Greatbatch Medical S.A., Orvin (CH); New Generation Devices, Inc., Glen Rock, NJ (US)

( * ) Notice: Subject to any disclaimer, the term of this patent is extended or adjusted under 35 U.S.C. 154(b) by 103 days.

(21) Appl. No.: 11/930,861

(22) Filed: Oct. 31, 2007

(65) Prior Publication Data

US 2008/0051791 A1 Feb. 28, 2008

Related U.S. Application Data

(63) Continuation of application No. 10/809,034, filed on Mar. 25, 2004, now Pat. No. 7,722,653.

(51) Int. Cl.
*A61B 17/80* (2006.01)
(52) U.S. Cl. ...................................... 606/286
(58) Field of Classification Search .............. 606/96, 606/280
See application file for complete search history.

(56) References Cited

U.S. PATENT DOCUMENTS

| 2,699,774 A | 1/1955 | Livingston |
| 3,552,389 A | 1/1971 | Allgover et al. |
| 3,659,595 A | 5/1972 | Haboush |
| 3,716,050 A | 2/1973 | Johnston |
| 3,824,995 A | 7/1974 | Getscher et al. |
| 3,842,825 A | 10/1974 | Wagner |

(Continued)

FOREIGN PATENT DOCUMENTS

DE  2806414 A1  10/1978

(Continued)

OTHER PUBLICATIONS

Brueckmann et al., Proximal Tibial Osteotomy, Orthopedic Clinics of North America, vol. 13, No. 1, (Jan. 1982), p. 3-16.

(Continued)

*Primary Examiner*—Thomas C Barrett
*Assistant Examiner*—Nicholas Woodall
(74) *Attorney, Agent, or Firm*—Michael F. Scalise (57) ABSTRACT

A bone plate(s) of complex form is provided, particularly suited to tibial plateau-leveling osteotomy and a distal femoral osteotomy. The bone plate has a main longitudinal axis, a bone-contacting bottom side (not shown) and a top side with at least three sets of overlapping holes which communicate through the plate from the top to the bottom side. The sets of overlapping holes define threaded apertures having multifaceted surfaces. When applied to a bone, two sets of such overlapping holes are located so as to lie on opposite sides of an osteotomy site and on the tibial plate; a third is aligned at approximately 60 degrees with the longitudinal axis. The configuration of this complex bone plate vary, depending on the physiology of the patient. An object of the invention is to provide an orthopedic surgeon greater flexibility of choice in that a threaded peg providing secure fixing can be positioned at any interval along the bone plate, including at its extreme ends or on its elbow.

26 Claims, 8 Drawing Sheets

U.S. PATENT DOCUMENTS

| | | | |
|---|---|---|---|
| 4,120,298 A | 10/1978 | Fixel | |
| 4,219,015 A | 8/1980 | Steinemann | |
| 4,403,606 A | 9/1983 | Woo et al. | |
| 4,408,601 A | 10/1983 | Wenk | |
| 4,409,973 A | 10/1983 | Neufeld | |
| 4,421,112 A | 12/1983 | Mains et al. | |
| 4,454,876 A | 6/1984 | Mears | |
| 4,493,317 A | 1/1985 | Klaue | |
| 4,498,601 A | 2/1985 | Fort | |
| 4,501,268 A | 2/1985 | Comparetto | |
| 4,502,474 A | 3/1985 | Comparetto | |
| 4,509,511 A | 4/1985 | Neufeld | |
| 4,513,744 A | 4/1985 | Klaue | |
| 4,545,876 A | 10/1985 | McGivern, Jr. | |
| 4,565,191 A | 1/1986 | Slocum | |
| 4,565,193 A | 1/1986 | Streli | |
| 4,611,581 A | 9/1986 | Steffee | |
| 4,662,891 A | 5/1987 | Noiles | |
| 4,677,973 A | 7/1987 | Slocum | |
| 4,696,290 A | 9/1987 | Steffee | |
| 4,762,122 A | 8/1988 | Slocum | |
| 4,790,297 A | 12/1988 | Luque | |
| 4,794,918 A | 1/1989 | Wolter | |
| 4,800,874 A | 1/1989 | David et al. | |
| 4,867,144 A | 9/1989 | Karas et al. | |
| 4,875,475 A | 10/1989 | Comte et al. | |
| 4,957,479 A | 9/1990 | Roemer | |
| 4,957,496 A | 9/1990 | Schmidt | |
| 4,957,497 A | 9/1990 | Hoogland et al. | |
| 4,959,065 A | 9/1990 | Arnett et al. | |
| 4,988,350 A | 1/1991 | Herzberg | |
| 5,002,544 A | 3/1991 | Klaue et al. | |
| 5,006,120 A | 4/1991 | Carter | |
| 5,015,248 A | 5/1991 | Burstein et al. | |
| 5,085,660 A | 2/1992 | Lin | |
| 5,087,260 A | 2/1992 | Fixel | |
| 5,160,271 A * | 11/1992 | Franks, Jr. | 439/92 |
| 5,176,679 A | 1/1993 | Lin | |
| 5,216,941 A | 6/1993 | Kolvereid | |
| 5,232,249 A | 8/1993 | Kolvereid | |
| 5,261,910 A | 11/1993 | Warden et al. | |
| 5,275,601 A | 1/1994 | Gogolewski et al. | |
| 5,304,180 A | 4/1994 | Slocum | |
| 5,324,290 A | 6/1994 | Zdeblick et al. | |
| 5,364,399 A | 11/1994 | Lowery et al. | |
| 5,601,553 A | 2/1997 | Trebing et al. | |
| 5,681,311 A * | 10/1997 | Foley et al. | 606/283 |
| 5,709,686 A | 1/1998 | Talos et al. | |
| 5,733,287 A | 3/1998 | Tepic et al. | |
| 5,741,258 A | 4/1998 | Klaue et al. | |
| 5,810,823 A | 9/1998 | Klaue et al. | |
| 5,851,207 A * | 12/1998 | Cesarone | 606/86 B |
| 5,968,047 A | 10/1999 | Reed | |
| 5,976,141 A | 11/1999 | Haag et al. | |
| 5,997,541 A | 12/1999 | Schenk | |
| 6,048,344 A | 4/2000 | Schenk | |
| 6,096,060 A | 8/2000 | Fitts et al. | |
| 6,206,881 B1 | 3/2001 | Frigg et al. | |
| 6,309,393 B1 | 10/2001 | Tepic et al. | |
| 6,331,179 B1 | 12/2001 | Freid | |
| 6,358,250 B1 | 3/2002 | Orbay | |
| 6,406,478 B1 | 6/2002 | Kuo | |
| 6,623,486 B1 | 9/2003 | Weaver et al. | |
| 6,669,701 B2 * | 12/2003 | Steiner et al. | 606/282 |
| 6,706,046 B2 | 3/2004 | Orbay et al. | |
| 6,719,759 B2 * | 4/2004 | Wagner et al. | 606/282 |
| 6,821,278 B2 | 11/2004 | Frigg et al. | |
| 7,063,701 B2 | 6/2006 | Michelson | |
| 7,090,676 B2 | 8/2006 | Huebner et al. | |
| D536,453 S * | 2/2007 | Young et al. | D24/155 |
| 2002/0045901 A1 | 4/2002 | Wagner et al. | |
| 2002/0156474 A1 | 10/2002 | Wack et al. | |
| 2002/0183752 A1 | 12/2002 | Steiner et al. | |
| 2003/0040748 A1 | 2/2003 | Aikins et al. | |
| 2004/0167522 A1 | 8/2004 | Niederberger et al. | |
| 2004/0181228 A1 | 9/2004 | Wagner et al. | |
| 2005/0015089 A1 * | 1/2005 | Young et al. | 606/69 |
| 2005/0216008 A1 | 9/2005 | Zwirnmann et al. | |
| 2005/0216009 A1 | 9/2005 | Michelson | |
| 2006/0212035 A1 | 9/2006 | Wotton, III | |
| 2006/0264946 A1 * | 11/2006 | Young | 606/69 |
| 2007/0016205 A1 * | 1/2007 | Beutter et al. | 606/69 |
| 2008/0039851 A1 * | 2/2008 | Schulz et al. | 606/87 |
| 2008/0045960 A1 * | 2/2008 | Bruecker et al. | 606/69 |

FOREIGN PATENT DOCUMENTS

| | | |
|---|---|---|
| DE | 0207884 | 3/1990 |
| DE | 4341980 | 6/1995 |
| DE | 4343117 | 6/1995 |
| EP | 0100114 | 2/1984 |
| EP | 0355035 | 2/1990 |
| FR | 2472373 | 7/1981 |
| FR | 2556583 | 6/1985 |
| FR | 2606268 | 5/1988 |
| WO | 0053110 | 9/2000 |
| WO | 0053111 | 9/2000 |
| WO | 0119267 | 3/2001 |
| WO | 0154601 | 8/2001 |
| WO | 0200127 | 1/2002 |
| WO | 02096309 | 12/2002 |
| WO | 2004089233 | 2/2004 |
| WO | 2005117732 | 12/2005 |

OTHER PUBLICATIONS

Sundaram et al., Dome Osteotomy of the Tibia for Osteoarthritis of the Knee, The Journal of Bone and Joint Surgery, vol. 68-B, No. 5, (Nov. 1986), p. 782-786.

Slocum et al, Tibial Plateau Leveling Osteotomy for Repair of Cranial Cruciate Ligament Rupture in the Canine, Veterinary Clinics of North America: Small Animal Practice, vol. 23, No. 4, (Jul. 1993), p. 777-795.

Reif et al, Effect of Tibial Plateau Leveling on Stability of the Canine Cranial Cruciate-Deficient Stifle Joint: an in Vitro Study, Veterinary Surgery, 31, (2002), p. 147-154.

Wheeler et al., In Vitro Effects of Osteotomy Angle and Osteotomy Reduction on Tibial Angulation and Rotation During the Tibial Plateau-Leveling Osteotomy Procedure, Veterinary Surgery, 32, (2003), p. 371-377.

Fettig et al., Observer Variability of Tibial Plateau Slope Measurement in 40 Dogs With Cranial Cruciate Ligament-Deficient Stifle Joints, Veterinary Surgery, 32, (2003), p. 471-478.

Miniaci et al., Proximal Tibial Osteotomy. A New Fixation Device, PubMed Article.

Lang et al., Cylindrical Osteotomy of the Upper End of the Tibia, PubMed Article.

Schneider et al., Cylindrical Osteotomy of the Upper Extremity of the Tibia with Advancement of the Patellar Ligament. Biomechanical Treatment of Gonarthrosis, PubMed Article.

Cassarino et al., High Domed Tibial Osteotomy in the Treatment of Angular Deviations of the Knee. A New System of Surgical Instrumentation, PubMed Article.

Soccetti et al., Domed High Tibial Osteotomy: the Long-Term Results in Tibiofemoral Arthritis with and without Malalignment of the Extensor Apparatus, PubMed Article.

Slocum et al., Current Techniques in Small Animal Surgery, Baltimore: Williams & Wilkins, TX-4-606-643, (1997), 1340 pages.

Slocum et al., Dog Trot, VAu-91-980, (1985).

Sundaram et al., Dome osteotomy of the tibia for osteoarthritis of the knee, PumMEd Article.

AXIS Fixation System by Sofamor Danek, published Feb. 1997, entire document.

* cited by examiner

FIG. 6

LOCKING BONE PLATE

CROSS-REFERENCE TO RELATED APPLICATIONS

This application is a continuation application of U.S. patent application Ser. No. 10/809,034, filed Mar. 25, 2004 now U.S. Pat. No. 7,722,653, the contents of which are incorporated herein by reference hereto.

BACKGROUND OF THE INVENTION

This invention relates to devices, implants and prostheses used in orthopaedic surgery, and, more particularly, to bone plates used to reinforce fractured bones and thus promote healing.

A compressive screw system, also known as the DCS system, is a bone plate system that has been used in trauma surgery for many years. The procedures for use of this system are well documented by the AO Institute, an institute having as one of its goals, the promotion of new orthopaedic surgical procedures. This system included a bone plate having slots communicating therethrough. A land in which the slot is wider at one end defines a stepped surface adjacent the portion of the slot that extends through the bone plate. The stepped surface is generally cut with a spherical endmill, thus creating a spherical stepped surface.

In a still further development, bone plates have been developed having individual threaded apertures and non-threaded apertures interspersed along the length of the plate. In this and other designs, the distance between holes has become a standard. Although an improvement over the inserts noted above, the locking positions are pre-defined, and only available in limited locations, which also reduce surgical flexibility. In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert designs rely on a friction lock via contact between two surfaces. Friction locks are not reliable and come lose more easily than threaded locked holes. The result of such a design is inferior to that of the threaded plate and screw designs discussed below.

In U.S. Pat. No. 5,002,544, there is shown an osteosynthetic pressure plate having a cross-section transverse to the longitudinal axis of the plate at least one point being wider toward the upper surface than toward the lower surface and the plate having recesses in the lower surface so that upon application to a bone there is space between the bone and the plate. The cross-section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

Further, U.S. Pat. No. 5,709,686 describes a bone plate that has recesses or reduced thickness portions on its sides, between threaded apertures. Although the purpose is not specifically described, these recesses appear to function to avoid warpage of the threaded portions when the bone plate is bent. However, when such a bone plate is fixed to a bone, these discontinuous recesses are exposed and may potentially come into contact with and potentially aggravate muscle tissue.

Still further, U.S. Pat. No. 5,733,287 shows, in FIG. 4, a plate that has transverse cuts 13 and a longitudinal cut 14 on the lower surface 7 to reduce contact between the plate and bone. Due to the transverse undercuts 13, the cross-section 15 between the holes is already significantly reduced and therefore is not further decreased by an additional groove 10 on the upper surface 6 as in the embodiment according to FIG. 3. To avoid a cross-section that is too thin, the groove 10 on the upper surface 6 is made discontinuous in short segmental grooves 16 providing a smooth transition into and out of the holes 8.

In yet another solution, PCT application no. WO01/54601 combines the features of the DCS system discussed above with a locking screw. This design combines the features of the DCS system with a locking screw. Such a system is known as the combi-slot. In this design, the stepped surface of the slot is generally to ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

Further, this combi-hole includes two distinct overlapping portions in a single slot. One portion of the slot is suited to receive a standard bone screw, while the other portion of the slot is suited to receive a threaded peg oriented perpendicular to the top surface of the bone plate. Also, the combi-holes are generally oriented with the threaded portions being on the innermost end of the combination and the unthreaded portions oriented toward the ends of the bone plate. This improvement increased the flexibility of choice available to orthopedic surgeons using the device in that it was more likely that a hole would be present at a suitable anchoring point in the bone plate. Nevertheless, there are often trauma situations that are best served by the threaded portion being at the extreme ends of the bone plate and/or at various positions throughout the plate. In addition, sometimes there is no specific center of the facture—in such a situation, use of the combi-hole design is limited.

While patent application no. WO01/54601 has proven advantageous because screws can be locked to the plate, the presence of an unthreaded slot limits the user's ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

U.S. Pat. No. 5,324,290 shows a complex bone plate having slots with countersunk circular recessed cut at intervals along the slot (a similar arrangement is shown in U.S. Pat. No. 4,696,290). It further shows the bone plate torqued against the bone so as to at least marginally, conform to the shape of the bone (see FIG. 2). Other patents of interest include U.S. Pat. Nos. 3,716,050, 3,659,595, 5,681,311, 5,261,910, and 5,364, 399, as well as German Patent application DE4341.980A1, all showing combinations of conventional slots and recesses which do not fully accommodate a bone screw having a threaded head.

In comparison with the combi-hole design and the friction locking design described above, what is needed is a bone plate that provides greater flexibility of choice to the surgeon. More specifically, what is needed is a bone plate that provides this choice of plate placement while reliably and permanently fixing the bone plate to the bone fragments, in any hole position.

What is needed is a bone plate that provides greater flexibility of choice to the surgeon, in a bone plate that has multiple orientations for the locking screw and thus, plate placement, while reliably and permanently fixing the bone plate to the bone fragments, in any hole position.

More specifically, what is needed is a bone plate that provides this choice while reliably and permanently fixing the bone plate to the bone fragments.

In addition, what is needed is a versatile bone plate having recesses which determine where the bone plate will bend, in order to avoid the threads in any holes to be bent or warped, while maintaining a smooth external surface.

Finally, what is needed is a bone plate with holes that create bi-directional compression.

SUMMARY OF THE INVENTION

A bone plate(s) of complex form is provided, particularly suited to tibial plateau-leveling osteotomy and a distal femoral osteotomy. The bone plate has a main longitudinal axis, a bone-contacting bottom side (not shown) and a top side with at least two sets of overlapping holes which communicate through the plate from the top to the bottom side. The sets of overlapping holes define threaded apertures having multifaceted surfaces. When applied to a bone, two sets of such overlapping holes are located so as to lie on opposite sides of an osteotomy site. Optionally, a third hole is aligned at approximately 60 degrees with the longitudinal axis. The configuration of this complex bone plate vary, depending on the physiology of the patient. An object of the invention is to provide an orthopaedic surgeon greater flexibility of choice in that a threaded peg providing secure fixing can be positioned at any interval along the bone plate, including at its extreme ends or on its elbow.

BRIEF DESCRIPTION OF THE DRAWINGS

FIG. 4b is a bottom perspective view of the alternate embodiment of FIG. 4a.

FIG. 5c is an alternate perspective top view of the embodiment of FIG. 5a.

DETAILED DESCRIPTION OF THE PREFERRED EMBODIMENT

Figure 1A:
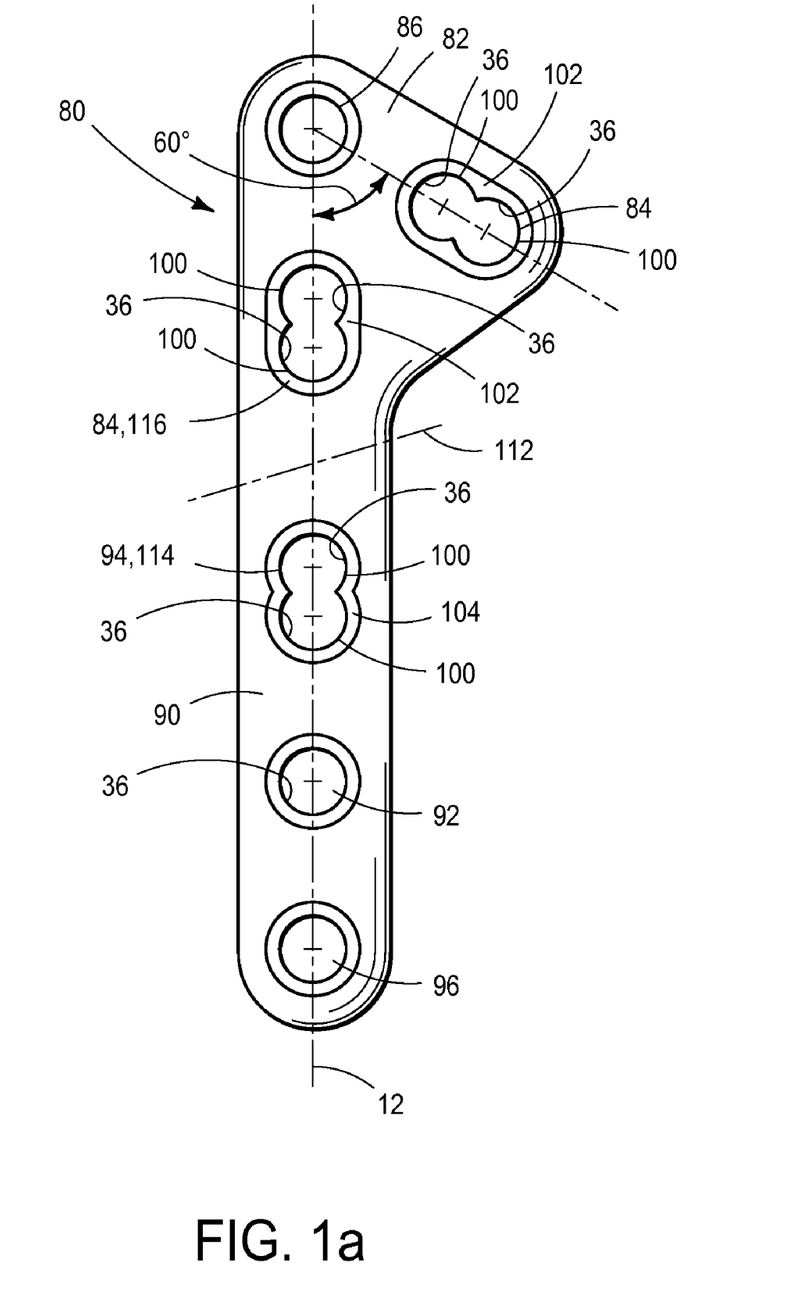
FIG. 1a is a top view an alternate embodiment suitable for tibial plateau-leveling osteotomy.

Referring now to FIG. 1a, a bone plate 80 of complex form is shown, particularly suited to tibial plateau-leveling osteotomy. The bone plate 80 has a main longitudinal axis 12, a bone-contacting bottom side (not shown) and a top side 16 with at least two sets of overlapping holes 100 which communicate through the plate from the top to the bottom side. The sets of overlapping holes 100 define threaded apertures having multifaceted surfaces 36. When applied to a bone, two sets of such overlapping holes 100 are located so as to lie on opposite sides of an osteotomy site 110. A third hole is aligned at approximately 60 degrees with the longitudinal axis 12, on the elbow portion.

The configuration of this complex bone plate 80 may vary, depending on the physiology of the patient. An illustration of the flexibility of application of the plate 80 is its flexible use in osteotomy.

The plate 80 has a flat triangular head 82 in which three spaced-apart apertures 84 and 86 are formed. The head 82 is integrally formed with an elongated lower portion 90 in which are located a plurality of apertures 92, 94 and 96, substantially co-axially with two of the apertures 84 and 86 in the head 82. Apertures 84 and 94 each consist of two overlapping holes 100 and a top lead-in feature which is either an elongated chamfer 102 or two overlapping chamfers 104.

Referring again to the triangular head 82, the apertures are arranged such that the aperture or hole 84 which is not axially aligned with the other apertures, is angled approximately 60 degrees from the longitudinal axis 12, which corresponds to a nominal angle of correction of the level of the tibial plateau. The osteotomy 110 (shown in FIG. 1b) is located approximately along the line 112, between the aperture designated 114 and the aperture designated 116. These apertures 114 and 116 are formed to enable compression of the fracture site across the line 112 when bone screws 24 having a bevelled surfaces 120 and 122 (preferably having no thread 30 on the head 26) enter the apertures and are torqued down such that wedging action takes place at the interface between the bevelled surfaces and the chamfered surfaces 102 and 104.

The aperture 116 has a chamfer 102 that allows a surgeon to insert a bone screw 24 (shown in FIG. 6) in the region between the holes 100 and not tighten completely, thus allowing movement along the long axis 12 and accurate placement of the bone plate 80 upon tightening. Note that aperture 114 may be used in a similar manner to aperture 116, the difference being that the form 104 of the chamfer does not allow for the placement of the screw 24 at any position along the length of the aperture (rather, there are only two possible positions: coaxial with the holes 100). The holes 92 and 96 may include threads 30 that are locking or non-locking, depending on the particular need of the surgeon.

Figure 1B:
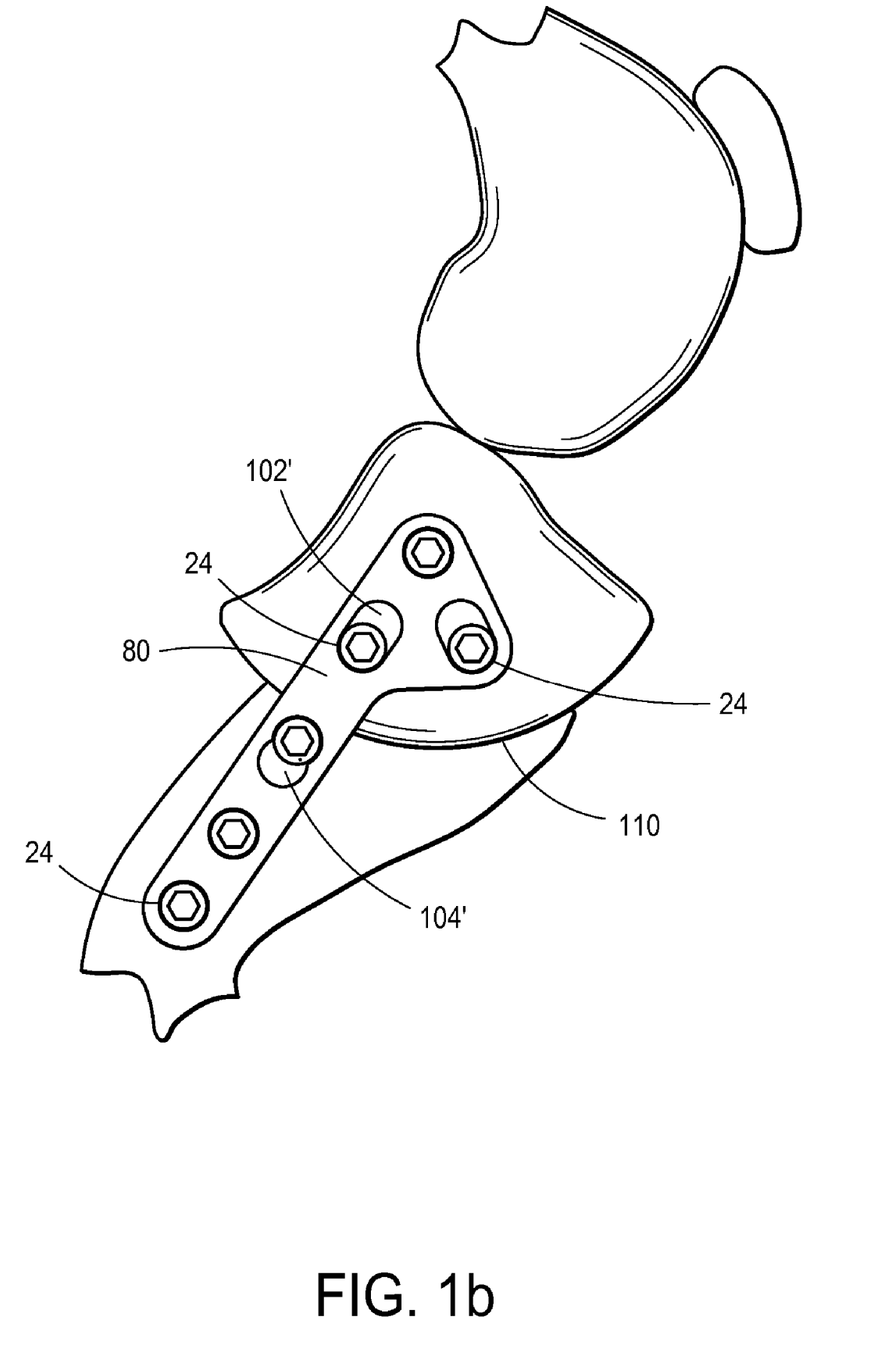
FIG. 1b is a view showing placement of the embodiment of FIG. 1a applied in tibial plateau-leveling osteotomy.

Referring now to FIG. 1b, application of the bone plate 80 is shown for tibial plateau-leveling osteotomy in a canine subject. It should be noted, however, that there are several suitable veterinary and human orthopaedic applications as well.

Figure 2:
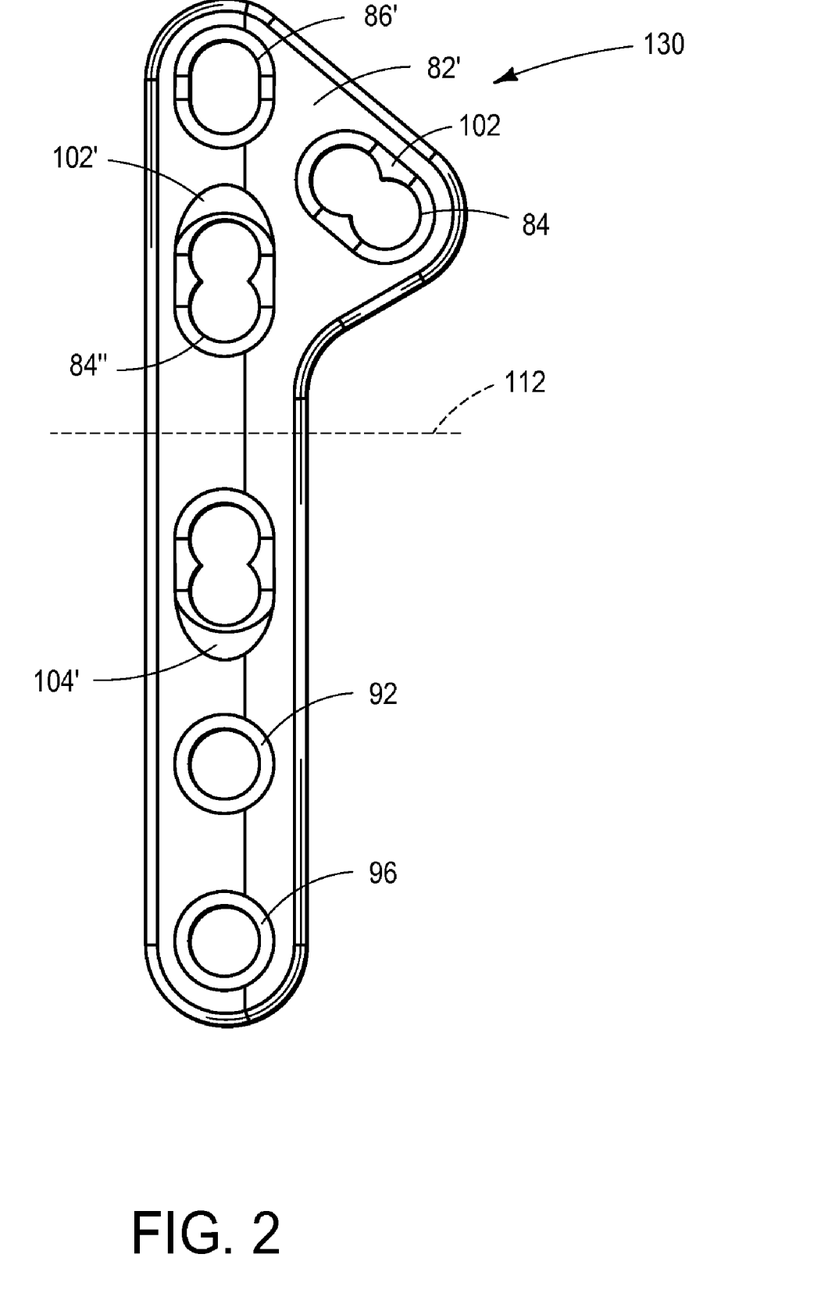
FIGS. 2 and 3 are top views of other alternate embodiments suitable for tibial plateau-leveling osteotomy.

Referring now to FIG. 2, an alternate embodiment 130 of the invention for this particular application shows typical modifications, such as longer chamfer surfaces 102' and 104' in the apertures 84' and 94' on either side of the osteotomy site. An elongated slot 86' in the flat, triangular head 82' includes a large underside chamfer (not shown) which permits greater bone screw angulation.

Figure 3:
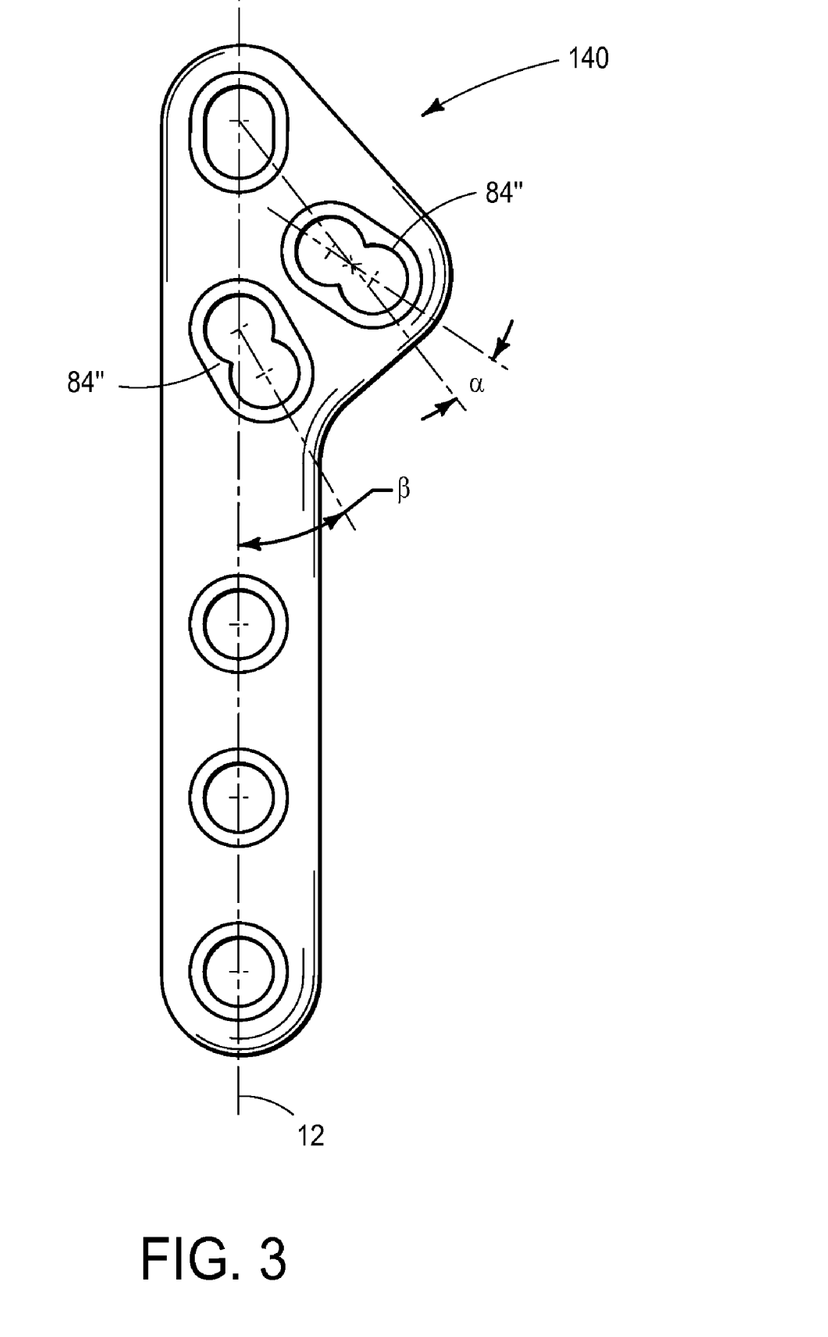

Referring now to FIG. 3, a second alternate embodiment 140 of the invention for this particular application shows other possible orientations of the apertures. For example, apertures 84" are oriented off axis in order to suit special cases.

Note that the threaded apertures 100 used in the invention provide hole centers located at specific locations (as opposed to apertures that are formed as a slot). Use of threads centered at a specific point allows the bone screw to be fixed at a specific location at which the surgeon may judge the bone structure to be best suited to support such a bone screw. Unlike designs using a slot, the apertures 100 of the invention eliminate wander of the screw in the aperture. This further permits placement at specific locations for buttressing and/or secure fixing in neutral screw loading areas.

Figure 4A:
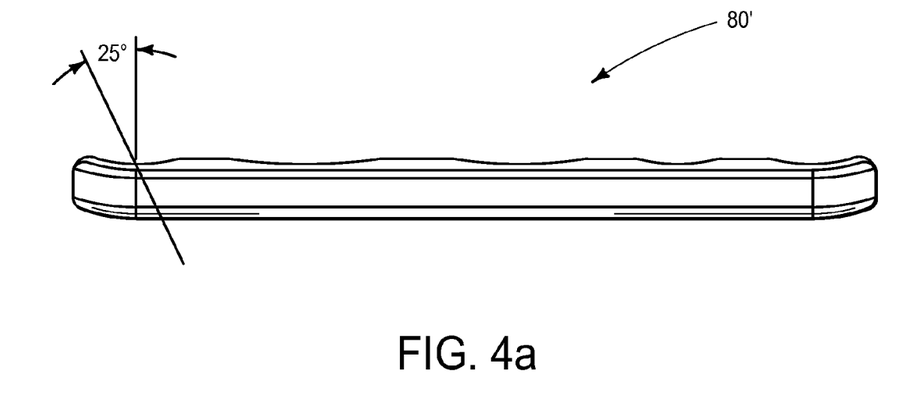
FIG. 4a is a top perspective view of another alternate embodiment of the bone plate.
Figure 4B:
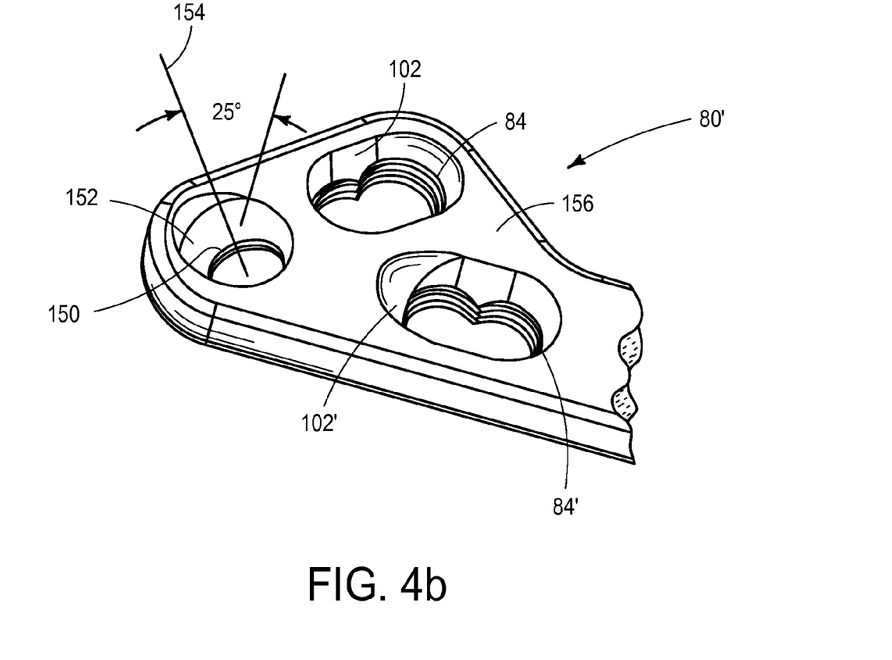
Figure 5A:
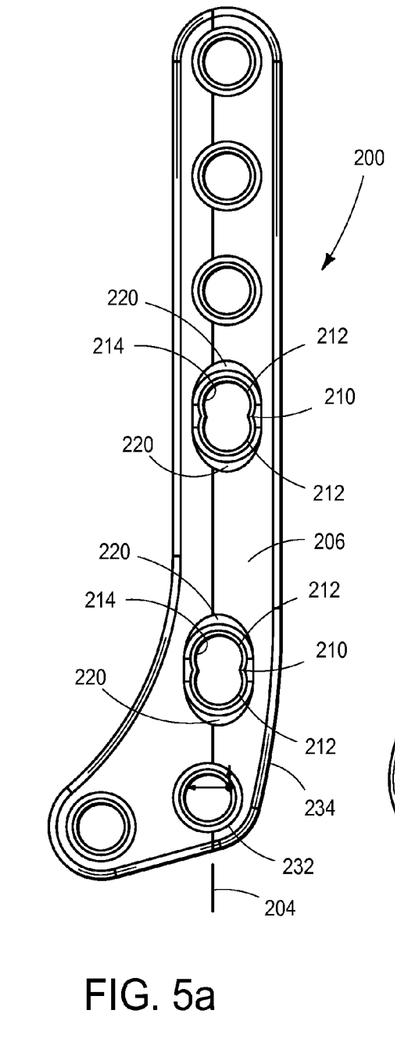
FIG. 5a is a top view of an alternate embodiment suitable for distal femoral osteotomies.
Figure 5B:
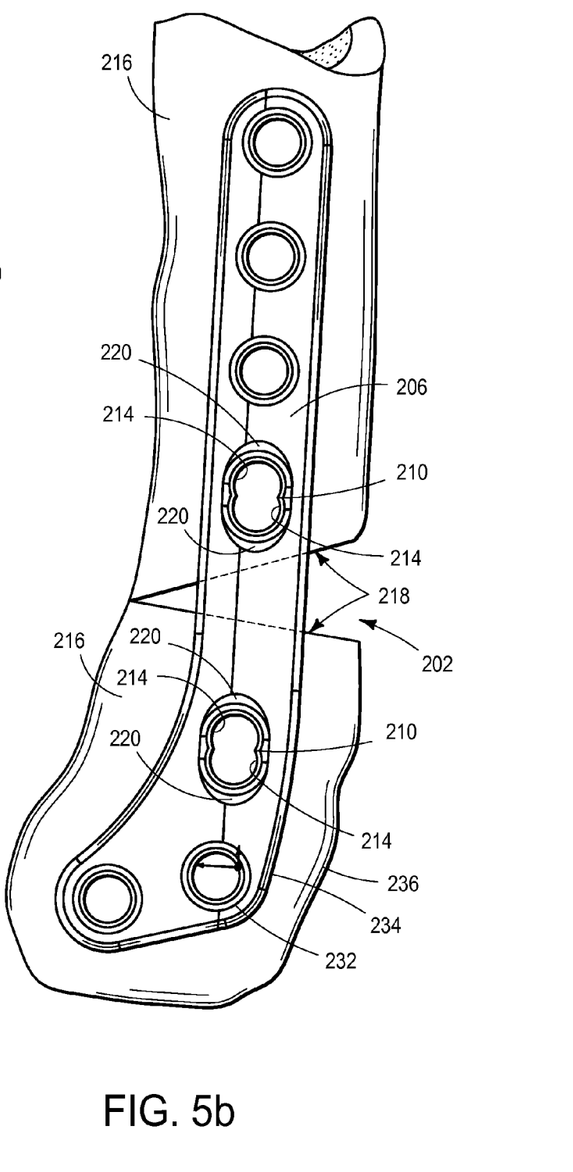
FIG. 5b is a view showing placement of the embodiment of FIG. 5a applied in a distal femoral osteotomy.
Figure 5C:
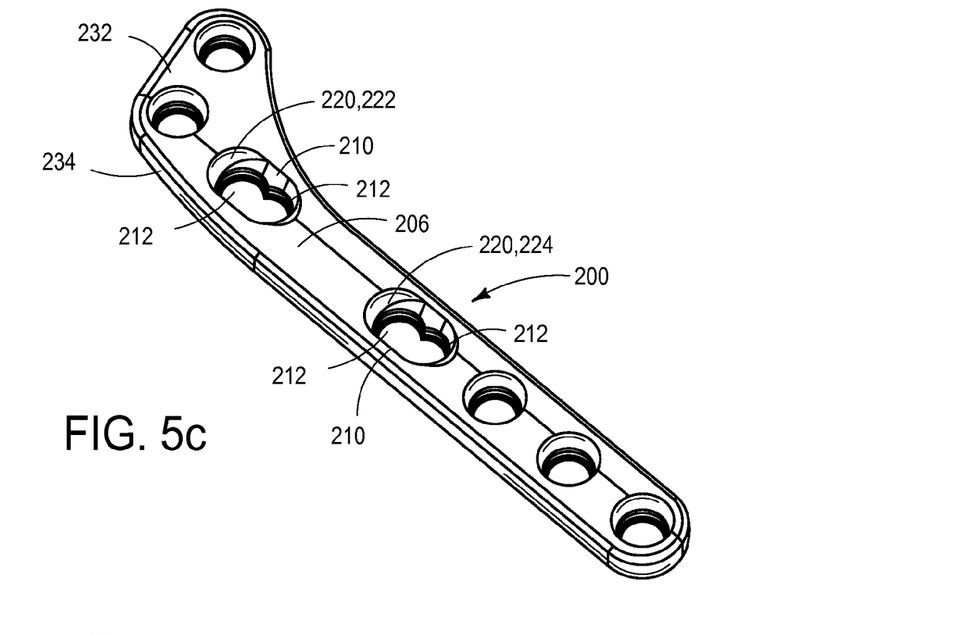
Figure 5D:
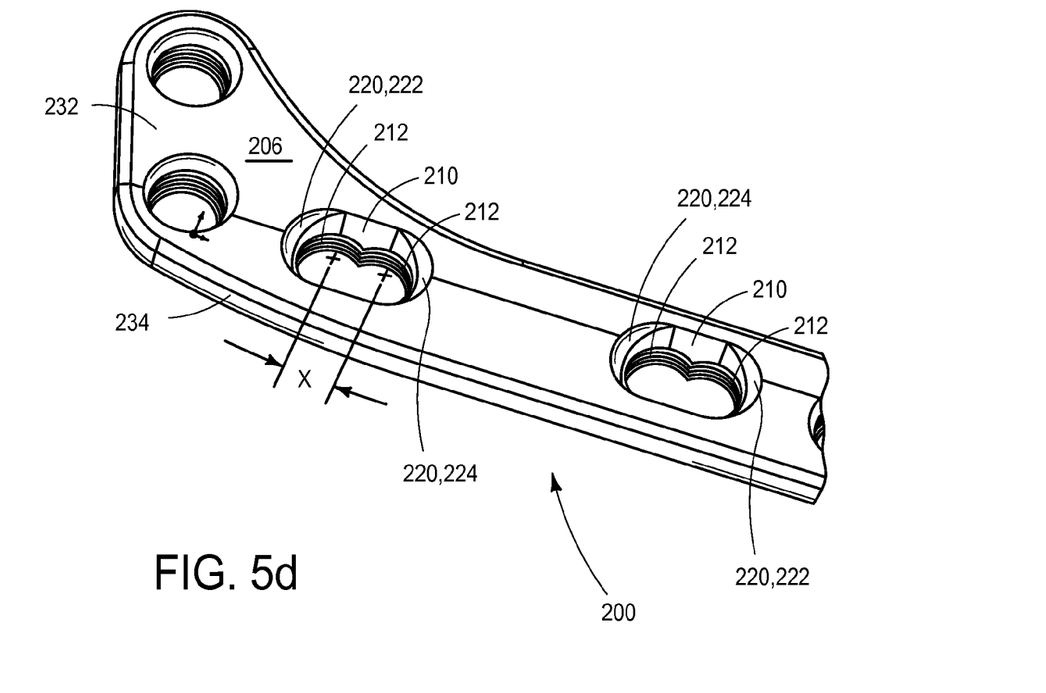
FIG. 5d is an alternate top view showing the positioning of compression holes with respect to the osteotomies.

Referring now to FIGS. 4a and 4b, in another embodiment, the bone plate 80' has a round hole 150 having a countersink 152 whose axis 154 is angled off of perpendicular from the top surface 156 of the bone plate and whose form corresponds to the shape of the head of a representative bone screw. The angle to from perpendicular is preferably 25 degrees as this angulation generally matches the amount which the plate 80' is contoured in situ. This angle allows screw placement that is parallel to the adjacent bone surface.

Referring now to FIGS. 5a-5d, in another embodiment, a bone plate 200 is particularly suited for distal femoral osteotomies 202 and correcting medial patellar luxations and/or other corrective osteotomies of the distal femur. The bone plate 200 has a main longitudinal axis 204, a bone contacting bottom side (not shown) and a top side 206 with at least two adjacent sets 210 of overlapping holes 212 which communicate through the plate from the top to the bottom side. The sets 210 of overlapping holes are compression holes which define threaded apertures 212 having multifaceted surfaces 214. When applied to a bone 216, two sets 210 of such overlapping holes 212 are located so as to lie on opposite sides 216 of an osteotomy site 202.

The threaded apertures 212 include wide bevels 220 on a far end 222 and near end 224 with respect to the osteotomy site.

The bone plate 200 further includes at least one locking bone peg (not shown) having an unthreaded body and threaded head which locks with the threads of a corresponding threaded aperture, thereby better ensuring rigid fixing of a fracture. Further, the distance X between the threaded apertures is defined to optimize either closing or opening of wedge femoral osteotomies 230. Preferably, the distance X is approximately 15 mm.

Optionally, a distal end 232 of the plate 200 forms a natural curve 234 corresponding to the shape 236 of the distal femur in order to minimize the potential of plate overhang.

In another feature, locking bone pegs 306 (shown in FIG. 6) interface with the threaded apertures. The threads cut in the head of these pegs are designed so as to lock with the threaded apertures in order to better ensure rigid fixing of a fracture when using pegs having a body without threads. The locking feature used can be any of the known methods of locking threads by mechanical means.

Figure 6:
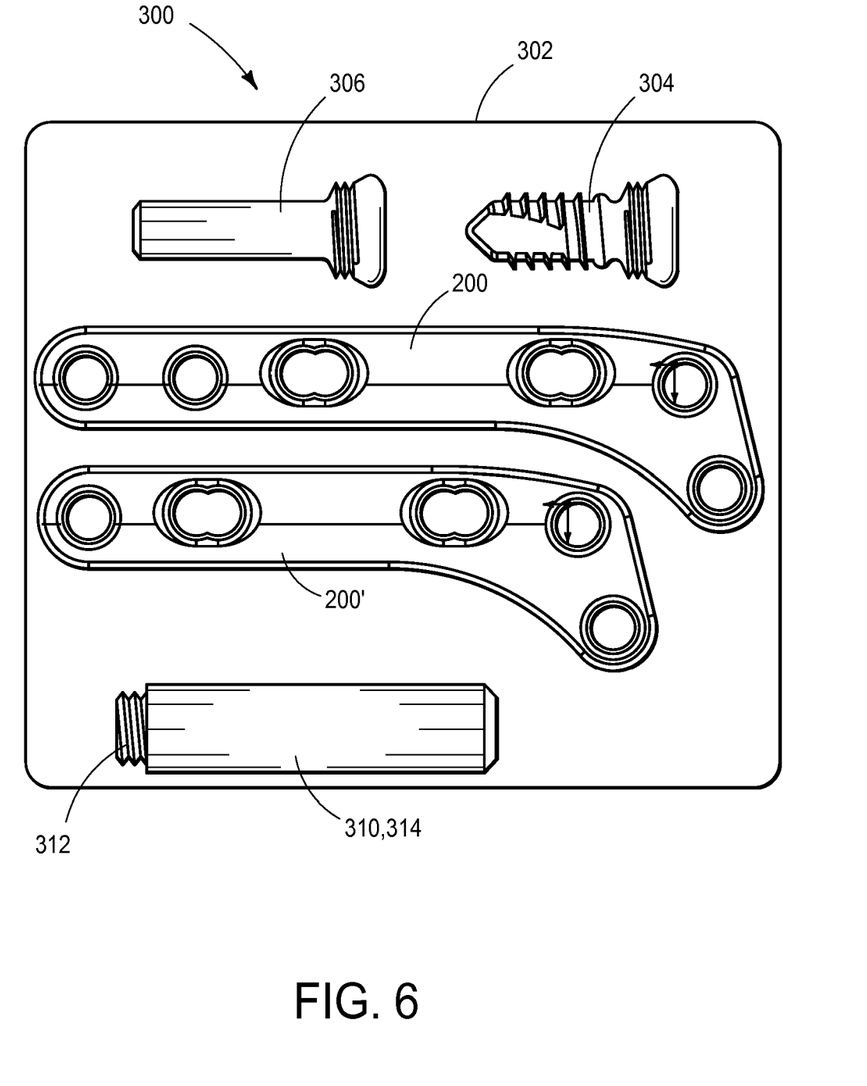
FIG. 6 is a top view of an orthopaedic kit of the invention.

Referring now to FIG. 6, in another embodiment, an orthopaedic kit 300 is provided which include a case 302, bone plates 200 and 200', a variety of bone screws 304, threaded pegs 306 of various lengths, and a drill guide 310. The drill guide 310 has a threaded end 312 that threads into the thread 40 of an overlapping hole 210. The drill guide 310 has a main drill guide surface 314 to securely hold the drill guide in a desired orientation with respect to the bone plate 200 in order to stabilize a drill (not shown) used in an orthopaedic procedure.

In an advantage of the invention, the bone plate 10 provides greater flexibility of choice to the surgeon in that a threaded peg providing secure fixing can be positioned at any interval along the bone plate, including at its extreme ends.

In another advantage, the bone plate 10 provides greater flexibility of choice by providing multiple overlapping holes 22 oriented (1) along the longitudinal axis 12 of the bone plate, (2) oriented at an angle ø to the longitudinal axis, and (3) staggered along the axis.

In still another advantage, the threaded apertures 40 of the bone plate 10 are provided with threads cut perpendicular to the top side 16 of the bone plate, as well as at an angle ø to normal.

In another advantage, the bone plates 80, 130, or 140 include features that further increase the adaptability of the invention to the particular needs of surgery, in this instance, tibial plateau-leveling osteotomy.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. An orthopedic kit including:
 a) a bone plate, which comprises:
  i) a head portion;
  ii) an elongated lower portion extending from the head portion, wherein the bone plate comprising the head portion and the elongated lower portion comprises a bone-contacting bottom side and a top side;
  iii) a first complex aperture located in the head portion, the first complex aperture comprised of two overlapping holes having an offset of a given distance between centers thereof, wherein the two overlapping holes of the first complex aperture extend along a first longitudinal axis and comprise a compression ramp extending from a first oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in either one or the other of the overlapping holes, wherein the first longitudinal axis bisects the first oval shaped opening along a greatest length thereof;
  iv) a second complex aperture located in the head portion, the second complex aperture comprised of two overlapping holes having an offset of a given distance between centers thereof, wherein the two overlapping holes of the second complex aperture extend along a second longitudinal axis and comprise a compression ramp extending from a second oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in either one or the other of the overlapping holes, wherein the second longitudinal axis bisects the second oval shaped opening along a greatest length thereof;

v) a third aperture located in the head portion; and vi) wherein the first longitudinal axis of the first complex aperture and the second longitudinal axis of the second complex aperture are angled with respect to each other and intersect at a center point of the third aperture; and b) at least one bone screw engageable with the apertures of the bone plate.

2. The kit of claim 1, further comprising a drill guide having a main drill guide surface and opposite end portions, one end portion of which is securely engageable with the female threaded surface of an aperture in the bone plate so as to securely hold the drill guide in a desired orientation with respect to the bone plate for stabilizing a drill used in an orthopedic procedure.

3. The kit of claim 1, wherein, when a bone plate is applied to a bone, at least one aperture is located so as to lie on one side of the osteotomy site and at least one complex aperture is located so as to lie on an opposite side of the osteotomy site.

4. The kit of claim 1 wherein the first and second longitudinal axes are at a 60° angle with respect to each other.

5. The kit of claim 1 wherein the oval shaped opening of the first complex aperture has a chamfered surface located at the top side of the bone plate.

6. The kit of claim 5 wherein the chamfered surface forms a portion of the one of the two overlapping holes of the first complex aperture that is spaced closest to the third aperture.

7. The kit of claim 1 wherein the third aperture is either circular or an elongated slot.

8. The kit of claim 1 wherein a fourth aperture is located in the elongated lower portion, the fourth aperture being comprised of two overlapping holes having an offset of a given distance between centers thereof, wherein the two overlapping holes of the fourth complex aperture extend along a fourth longitudinal axis and comprise a compression ramp extending from a fourth oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of the corresponding bone screw in either one or the other of the overlapping holes.

9. The kit of claim 8 wherein the fourth longitudinal axis bisects the fourth oval shaped opening along a greatest length thereof.

10. The kit of claim 8 wherein the first and fourth longitudinal axes are aligned with each other.

11. The kit of claim 8 wherein the oval shaped opening of the fourth complex aperture has a chamfered surface located at the top side of the bone plate.

12. The kit of claim 11 wherein the chamfered surface forms a portion of the one of the two overlapping holes of the fourth complex aperture that is spaced furthest from the third aperture.

13. The kit of claim 8 wherein the aligned first and fourth longitudinal axes of the respective first and fourth complex apertures and the second longitudinal axis of the second complex aperture intersect at a center point of the third aperture.

14. An orthopedic kit including:

a) a bone plate, which comprises:

i) bone-contacting bottom side and a top side;

ii) a first complex aperture and a second complex aperture, each comprised of two overlapping holes having an offset of a given distance between centers thereof, wherein the two overlapping holes of both the first and second complex apertures extend along respective first and second longitudinal axes and comprise a compression ramp extending from respective oval shaped openings at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in either one or the other of the overlapping holes, wherein the first and second longitudinal axes bisect the first and second oval shaped openings along a greatest length thereof;

iii) a third aperture; and iv) wherein the first longitudinal axis of the first complex aperture and the second longitudinal axis of the second complex aperture are angled with respect to each other; and b) at least one bone screw engageable with the apertures of the bone plate.

15. The kit of claim 14 wherein at least one of the first and second longitudinal axes passes through a center point of the third aperture.

16. The kit of claim 14 wherein neither of the first and second longitudinal axes pass through a center point of the third aperture.

17. The kit of claim 14 wherein the first and second longitudinal axes are at a 60° angle with respect to each other.

18. The kit of claim 14 wherein the oval shaped opening of the first complex aperture has a chamfered surface located at the top side of the bone plate.

19. The kit of claim 18 wherein the chamfered surface forms a portion of the one of the two overlapping holes of the first complex aperture that is spaced closest to the third aperture.

20. The kit of claim 14 wherein the third aperture is either circular or an elongated slot.

21. The kit of claim 14 wherein the third aperture is either circular or an elongated slot.

22. The kit of claim 14 further comprising a fourth aperture comprised of two overlapping holes having an offset of a given distance between centers thereof, wherein the two overlapping holes of the fourth complex aperture extend along a fourth longitudinal axis and comprise a compression ramp extending from a fourth oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of the bone screw in either one or the other of the overlapping holes.

23. The kit of claim 22 wherein the first and fourth longitudinal axes of the respective first and fourth complex apertures are aligned with respect to each other.

24. The kit of claim 22 wherein the second and fourth longitudinal axes of the respective second and fourth complex apertures are angled with respect to each other.

25. The kit of claim 22 wherein the oval shaped opening of the fourth complex aperture has a chamfered surface located at the top side of the bone plate.

26. The kit of claim 25 wherein the chamfered surface forms a portion of the one of the two overlapping holes of the fourth complex aperture that is spaced furthest from the third aperture.

* * * * *